(12) United States Patent
Song et al.

(10) Patent No.: US 6,737,065 B2
(45) Date of Patent: May 18, 2004

(54) METHOD FOR PRODUCING MUSHROOM MYCELIA AND USES THEREOF

(75) Inventors: Jae-Mahn Song, #B-401, Songnae APT, 558 Songnae-2-dong, Sosa-gu, Bucheon-city, 422-042 Kyunggi-do (KR); Se-Youn Han, Incheon (KR); Yun-Sun Na, Seoul (KR)

(73) Assignees: Jae-Mahn Song, Bucheon (KR); C.A. Biotech Co., Ltd., Bucheon (KR)

( * ) Notice: Subject to any disclaimer, the term of this patent is extended or adjusted under 35 U.S.C. 154(b) by 123 days.

(21) Appl. No.: 09/971,002

(22) Filed: Oct. 5, 2001

(65) Prior Publication Data

US 2003/0208796 A1 Nov. 6, 2003

(30) Foreign Application Priority Data

| Oct. 6, 2000 | (KR) | 2000-0058806 |
| Jun. 21, 2001 | (KR) | 2001-0035248 |
| Jun. 21, 2001 | (KR) | 2001-0035250 |

(51) Int. Cl.[7] ............................................. A61K 35/84
(52) U.S. Cl. ................................. 424/195.15; 514/866
(58) Field of Search ................... 514/866; 424/195.15; 426/2, 443, 807, 806

(56) References Cited

U.S. PATENT DOCUMENTS 6,569,475 B2 * 5/2003 Song et al.

FOREIGN PATENT DOCUMENTS

| CN | 1097025 | * | 1/1995 |
| CN | 1100587 | * | 3/1995 |
| CN | 1194790 | * | 10/1998 |
| EP | 1 106 599 | | 6/2001 |
| WO | WO 01/65029 | | 2/2001 |

* cited by examiner

*Primary Examiner*—Christopher R. Tate
(74) *Attorney, Agent, or Firm*—Nath & Associates PLLC; Gary M. Nath; Lee C. Heiman

(57) ABSTRACT

A method for producing mushroom mycelia and uses of the mushroom mycelia. Mushroom mycelia can be cultured at low cost in a broth made of the water from the washing of grains. Also, mushroom mycelia rich in trace minerals can be cultured in a broth supplemented with trace minerals. Feeding of feedstuffs mixed with the mushroom mycelia culture produces duck meats with excellent taste and quality and low cholesterol content.

1 Claim, 2 Drawing Sheets

METHOD FOR PRODUCING MUSHROOM MYCELIA AND USES THEREOF

BACKGROUND OF THE INVENTION

1. Field of the Invention

The present invention relates to a method for producing mushroom mycelia. More particularly, the present invention relates to production of mushroom mycelia by use of water from the washing of grains (hereinafter just as grain-washing water) as a culture medium, and by use of trace minerals as nutrient additives for the culture medium. Also, the present invention is concerned with the use of the mushroom cultures in raising ducks.

2. Description of the Prior Art

For their medicinal or healthful effects, many mushrooms have attracted keen attention. At present, mushroom mycelia for use in materials for medicines and foods are extensively produced in many countries through broth culture. For instance, *Tremella auranita* is cultured in broths and commonly used as an additive for walnut confectionery, crackers, breads, and beverages in China. More medicinal components from mushroom mycelia have been developed in Japan. Krestin (PS-K) obtained from mycelium cultures of *Coriolus versicolor* by hot water extraction, sizofilan obtained from mycelium cultures of *Schizophyllum commune*, and lentinan from *Lentinus edodes* have been commercialized as antitumor active materials. In Korea, mycelia obtained from *Ganoderma lucidum, Coriolus versicolor, Phellinus Linteus*, and *Cordyceps sinensis* are developed into materials for beverages and cosmetics.

However, such medicinally useful mushroom mycelia are produced at relatively high cost, although such costs have been gradually reduced. For example, the culture media are very expensive. Therefore, there remains a need for an improved method or system that can culture such medicinal mushroom mycelia effectively and at low cost.

In addition to medicinal/anti-tumorigenic polysaccharides, trace minerals such as chrome, selenium and germanium are found in mushrooms. As their effects on the physiology of the human body have been revealed, trace minerals are now regarded as important immunological and medicinal components. In fact, humans or animals deficient in trace minerals are apt to become diseased. For example, diabetic mellitus is aggravated by insufficient chrome or zinc, because the minerals provide environments necessary for the activity of insulin, thereby improving the medicinal effect of insulin. Found abundantly in yeast, chromium is the central atom in the glucose tolerance factor (GTF), which works with insulin to transport glucose from the blood into body cells, regulating blood sugar levels. Lack of selenium may be a cause of cancer and is also found to deepen senility and cause arteriosclerosis. Since the finding that medicinally useful plants such as ginseng and wild ginseng are rich in germanium, this trace mineral has been extensively studied for use in antitumor agents, hepatitis medications, and functional foods for immunity enhancement.

Fewer minerals are found in soils which have been treated with chemical fertilizers for long time periods. At present, yeasts are utilized as sources of chromium, selenium and germanium. Additionally, extensive attention is paid to mushrooms such as *Ganoderma lucidum* and *Coriolus versicolor* because of their richness in trace minerals such as chromium, selenium and germanium. Therefore, mushroom mycelia can be exploited as biomaterials for health foods, functional foods and medicines because they contain anti-tumorigenic polysaccharides and trace minerals.

Recent, it has been reported that pigs raised with feedstuff containing chromium picolinate grow fast, with an increase in muscle and a decrease in body fat. The same was found to be true of mice. There is possibility that other animals can be raised with the same effects when fed with chromium.

SUMMARY OF THE INVENTION

Leading to the invention, the intensive and thorough research into mushroom mycelium culture, conducted by the present inventors aiming to reduction in production cost, resulted in the finding that mushroom mycelia can be effectively grown in broths containing the water from the washing of grains, such as rice, glutinous rice, barley, wheat, millet, glutinous sorghum, glutinous hog millet, and Job's-tears. Addition of trace minerals to a culture broth made mushroom mycelia rich in the minerals. It was also found that, when being raised with feedstuffs added with the mushroom culture, ducks give delicious meats, which was also rich in nutrients.

It is therefore an object of the present invention to provide a method for culturing mushroom mycelia at low production cost with efficiency.

It is another object of the present invention to provide beverages with medicinal or healthful functionality.

It is a further object of the present invention to provide a method for raising ducks producing high quality meats.

DETAILED DESCRIPTION OF THE INVENTION

In the present invention, mushroom mycelia are cultured in a broth made of the water from the washing of a grain, such as rice, glutinous rice, barley, wheat, millet, glutinous sorghum, glutinous hog millet, or millet. This method is advantageous in that mushroom mycelia can be produced at low cost.

Also, mushroom mycelia are cultured in a broth supplemented with trace minerals such as chromium, selenium, and germanium. In this regard, the mushroom mycelia rich in trace minerals are produced.

Ducks, which have been fed with the mushroom mycelia culture, give high quality meats with good taste and low cholesterol content.

Below, culturing of mushroom mycelia will be described in conjunction with the accompanying drawings.

First Step: Seed Culture for Mushroom Mycelia

The seed culture is achieved by inoculating mushroom mycelia on agar plates or in broths.

Second Step: Preparation of Media for Culturing Mushroom Mycelia

PREPARATIVE EXAMPLE 1

Figure 1:
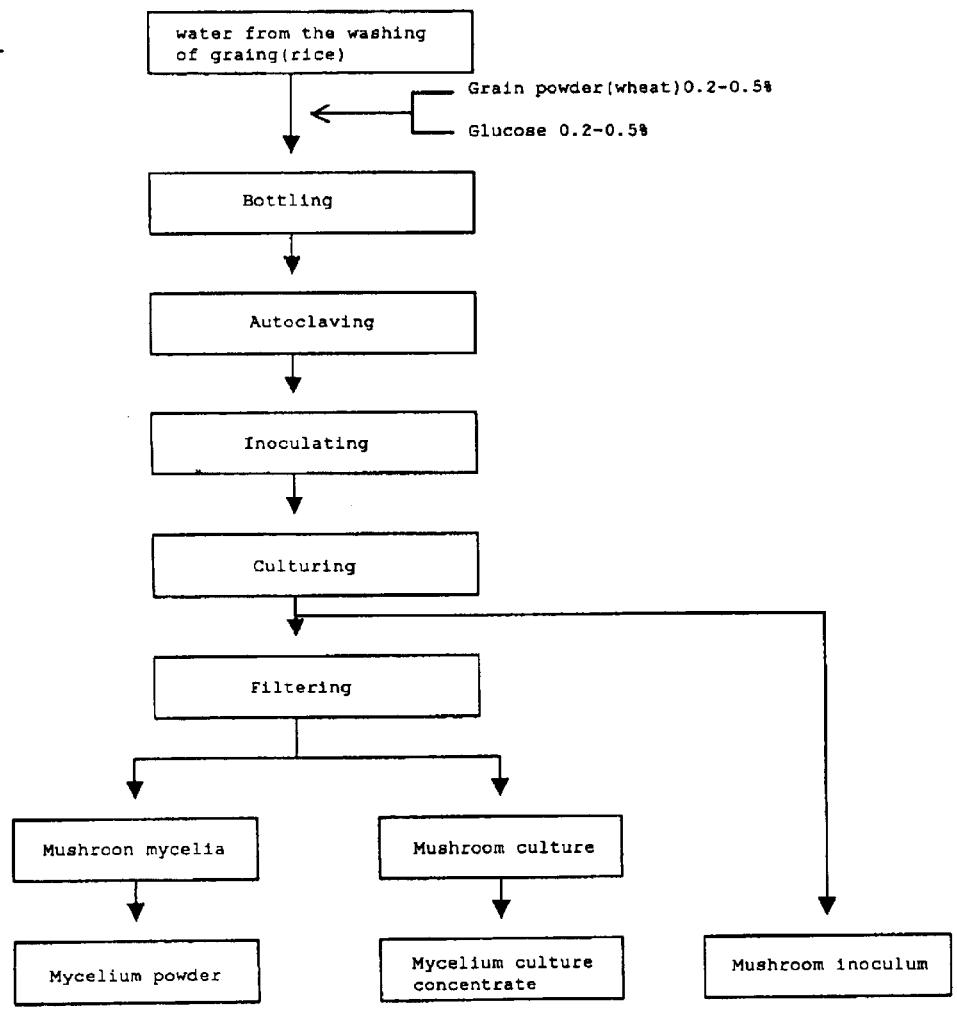
FIG. 1 is a flow chart illustrating the culturing of mushroom mycelia using the water from the washing of grains.

Culturing Process of Mushroom Mycelia Using the Water from the Washing of Grains To water from the first and/or second washing of rice, rice powder and glucose are added in an amount of 0.2 to 0.5%, each, as shown in FIG. 1. The mixture is poured into a culture vessel which is then sealed and sterilized by autoclaving for 20 min.

Instead of the water from the washing of rice, water from the washing of glutinous rice, barley, wheat, millet, glutinous sorghum, glutinous hog millet, or Job's-tears may be used. Water from the washing of rice may be easily obtained from houses or rice-packing factories. Effective for the culture of mushroom mycelia is the water from the first or second washing of grains. If the second washing is included, the total washing water can be harvested in amounts 5–10 times greater than the weight of the washed rice. Harvested water from the washing of grains can be used as a culture medium for mushroom mycelia after being autoclaved. According to mushroom strains, grain powders and glucose may be used in an amount of 0.2 to 2%, each, based on the weight of the medium, and preferably in an amount of 0.2 to 0.5%.

PREPARATIVE EXAMPLE 2

Culturing Process of Mushroom Mycelia Rich in Trace Minerals

Figure 2:
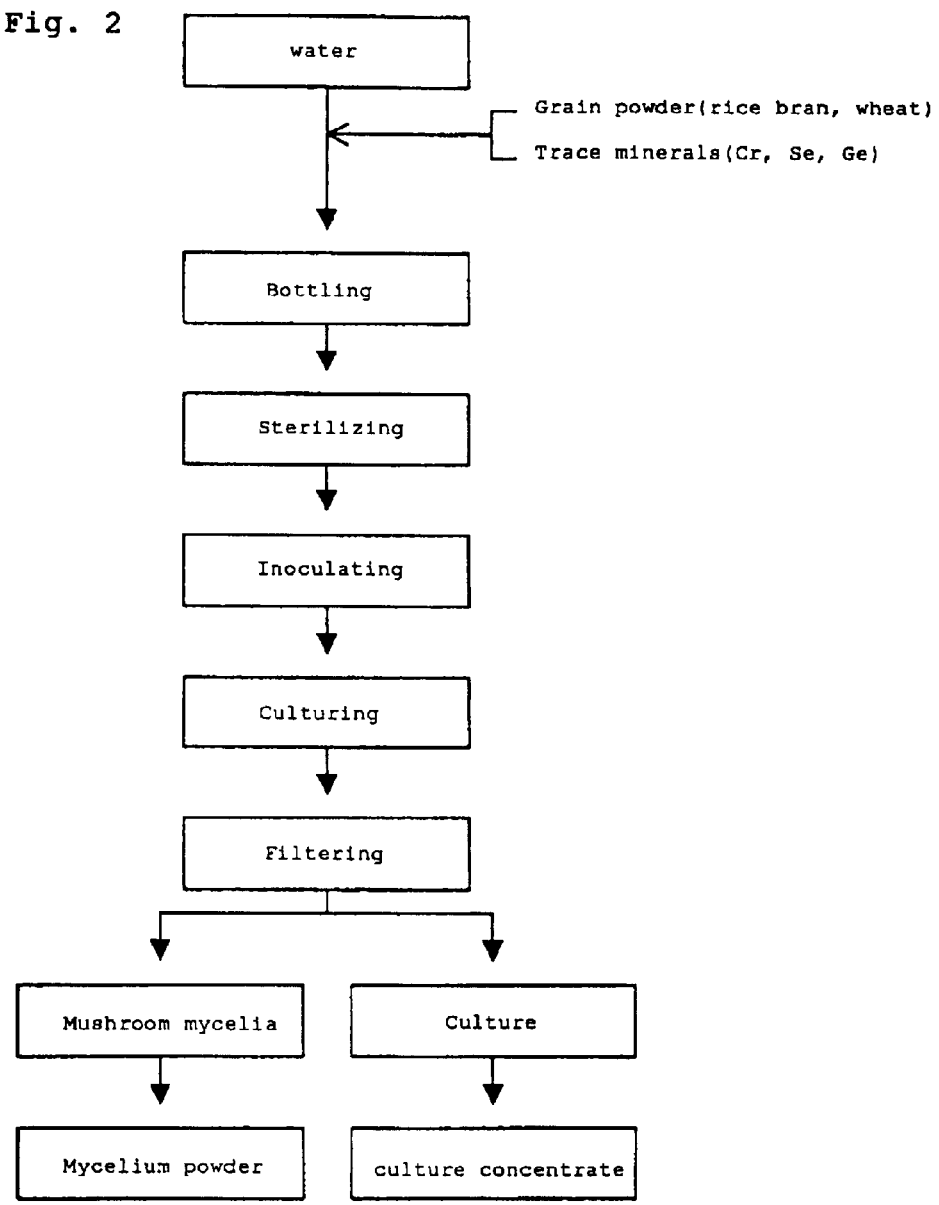
FIG. 2 is a flow chart illustrating the culturing of mushroom mycelia rich in trace minerals.

To water are added rice bran and wheat powder in an amount of 0.5%, each, followed by the addition of a trace mineral such as chromium, as shown in FIG. 2. The resulting solution is poured into a culture vessel, sealed and autoclaved for 20 min.

Instead of chromium, selenium or germanium may be used. According to mushroom strains, chromium ($CrCl_3$) is added in an amount of 100 to 1,200 mg/L, selenium ($Na_2SeO_3$) in an amount of 20 to 300 mg/L, and germanium ($GeO_2$) in an amount of 200 to 1,2000 mg/L. Preferable amounts are 200 mg/L of chromium, 500 mg/L of selenium, and 1,000 mg/L of germanium.

Third Step: Culturing of Mushroom Mycelia

After being cooled, the sterilized medium prepared in the second process is aseptically inoculated with the mushroom seed cultured in the first process. Culturing is conducted in a culture room maintained at 20 to 30° C. for 10 to 20 days without shaking and for 5 to 10 days with shaking.

Exemplified by *Coriolus versicolor, Ganoderma lucidum, Schizophyllum commune, Peurotus ostreatus, Peurotus sajor-caju, Lentinus edodes* (Berk), *Flammulina velutipes, Auricularia* spp., and *Pholiota nameko*, any mushroom may be used in the present invention if it is edible and has medicinal properties.

Fourth Step: Preparation of Mushroom Seed Strain, Mycelium Culture Extract, and Mycelium Powder The culture grown in the third process may be used as a seed culture. For the preparation of mycelium culture extract, the culture is filtered and the filtrate is concentrated under vacuum or by heating. From the culture are recovered only the mycelia, which are then dried at 50 to 60° C. for 12 to 24 hours to give mycelium powder.

The mycelium powder can be utilized for the preparation of functional foods and medicines. Meanwhile, the culture extract may be added to feedstuffs. In the mycelia recovered, trace minerals such as chromium, selenium and germanium, and anti-tumorigenic polysaccharides such as exopolysaccharides and β-D-glucan, are present. The mycelium culture contains scores of hydrolytic enzymes, such as cellulases, laccases, lipases, polygalactouronases, proteases, and the like, and their lysates, in addition to the anti-tumorigenic polysaccharides such as exopolysaccharides and β-D-glucan. Further, deodorizing components are found in the mycelium culture. Therefore, the mycelium powder and the mycelium culture can be used for the preparation of functional foods, medicines, and feedstuffs.

For the preparation of functional beverages, as mentioned above, the mushroom mycelia obtained according to the present invention can be used. For example, 1 to 10 g and preferably 3 g of the *Ganoderma lucidum* mycelium powder prepared by use of a broth added with chromium is mixed with 0.01 to 1 g and preferably 0.15 g of the *Ganoderma lucidum* mycelium powder prepared by use of a broth added with selenium in 1 to 2 liters and preferably 1.5 liters of the *Ganoderm lucidum* culture obtained by use of a broth added with no trace minerals and the mixture was concentrated and filtered. Of course, additives usually used for preparation of beverages, such as glucose, maltose, saccharose, oligosaccharides, natural honey, and the like, may be added when a beverage is made of the culture and mushroom mycelia. In this regard, the mushroom mycelia containing trace minerals are preferably used in an amount of 0.001 to 1% by weight based on the total weight of the beverage.

In accordance with the present invention, the mycelium culture is used for the raising of ducks. When ducks have been fed with feedstuffs mixed with the mycelium culture, the duck meats are found to contain chromium in an amount of 0.08 to 0.4 mg/kg and selenium in an amount of 0.3 to 1.0 mg/kg.

A better understanding of the present invention may be obtained in light of the following examples which are set forth to illustrate, but are not to be construed to limit the present invention.

In the following examples, mushroom mycelia were cultured by use of water from the washing of rice, glutinous rice, barley, wheat, millet, glutinous sorghum, glutinous hog millet, and Job's tears.

EXAMPLE 1

Culturing of *Coriolus versicolor* by Use of Rice-Washing Water and Processing of the Culture To 2 liters of the water from the first and second washing of rice, wheat powder and glucose were added in an amount of 0.2 to 0.5%, each. The resulting solution was sterilized by autoclaving for 20 min. Into the sterilized broth were aseptically inoculated *Coriolus versicolor* seed fungi, followed by fix incubation at 25° C. for 15 days. Thereafter, the mycelia were harvested by filtration and dried with hot wind to obtain 8 g of mycelium powder. The filtrate, which was up to 1.8 liters, was concentrated to 900 mL by heating at 100° C. for 1 hour.

EXAMPLE 2

Culturing of *Coriolus versicolor* by Use of Glutinous Rice-Washing Water and Processing of the Culture Using the water from the washing of glutinous rice, a culture medium was prepared and used to produce a powder of *Coriolus versicolor* mycelia and a concentrate of a *Coriolus versicolor* culture in a manner similar to that of Example 1. The powder and the concentrate were 6 g and 920 mL, respectively.

EXAMPLE 3

Culturing of *Coriolus versicolor* by Use of Barley-Washing Water and Processing of the Culture Using the water from the washing of barley, a culture medium was prepared and used to produce a powder of *Coriolus versicolor* mycelia and a concentrate of a *Coriolus versicolor* culture in a manner similar to that of Example 1. The powder and the concentrate were 9 g and 880 mL in mass and volume, respectively.

EXAMPLE 4

Culturing of *Coriolus versicolor* by Use of Wheat-Washing Water and Processing of the Culture Using the water from the washing of wheat, a culture medium was prepared and used to produce a powder of Coriolus versicolor mycelia and a concentrate of a Coriolus versicolor culture in a manner similar to that of Example 1. The powder and the concentrate were 8 g and 900 mL in mass and volume, respectively.

EXAMPLE 5

Culturing of Coriolus versicolor by Use of Millet-Washing Water and Processing of the Culture Using the water from the washing of millet, a culture medium was prepared and used to produce a powder of Coriolus versicolor mycelia and a concentrate of a Coriolus versicolor culture in a manner similar to that of Example 1. The powder and the concentrate were 7 g and 910 mL in mass and volume, respectively.

EXAMPLE 6

Culturing of Coriolus versicolor by Use of Glutinous Sorghum-Washing Water and Processing of the Culture Using the water from the washing of glutinous sorghum, a culture medium was prepared and used to produce a powder of Coriolus versicolor mycelia and a concentrate of a Coriolus versicolor culture in a manner similar to that of Example 1. The powder and the concentrate were 6 g and 920 mL in mass and volume, respectively.

EXAMPLE 7

Culturing of Coriolus versicolor by Use of Glutinous Hog Millet-Washing Water and Processing of the Culture Using the water from the washing of glutinous hog millet, a culture medium was prepared and used to produce a powder of Coriolus versicolor mycelia and a concentrate of a Coriolus versicolor culture in a manner similar to that of Example 1. The powder and the concentrate were 7 g and 910 mL in mass and volume, respectively.

EXAMPLE 8

Culturing of Coriolus versicolor by Use of Job's Tears-Washing Water and Processing of the Culture Using the water from the washing of Job's tears, a culture medium was prepared and used to produce a powder of Coriolus versicolor mycelia and a concentrate of a Coriolus versicolor culture in a manner similar to that of Example 1. The powder and the concentrate were 9 g and 880 mL in mass and volume, respectively.

Mushroom mycelia were cultured in media supplemented with chromium, selenium and germanium and measured for mineral contents.

EXAMPLE 9

Culturing of Mushroom Mycelia in Media Supplemented with Chromium and Processing of the Culture To 2 liters of water, rice bran and wheat powder were added in an amount of 0.5%, each, followed by the addition of chromium ($CrCl_3$) at an amount of 200 mg/L. After being autoclaved for 20 min, the medium was aseptically inoculated with Coriolus versicolor. The fungi were cultured at 25° C. for 15 days, after which the mycelia were harvested by filtration and dried with hot wind to obtain 6 g of mycelium powder. The filtrate, which was up to 1.8 liters, was concentrated to 900 mL by heating at 100° C. for 1 hour.

EXAMPLE 10

Culturing of Mushroom Mycelia in Media Supplemented with Selenium and Processing of the Culture A culture medium was prepared using 50 mg/L of selenium ($Na_2SeO_3$) and used to produce a powder of Coriolus versicolor mycelia and a concentrate of a Coriolus versicolor culture in a manner similar to that of Example 9. The powder and the concentrate were 6.5 g and 880 mL in mass and volume, respectively.

EXAMPLE 11

Culturing of Mushroom Mycelia in Media Supplemented with Germanium and Processing of the Culture A culture medium was prepared using 1,000 mg/L of germanium ($GeO_2$) and used to produce a powder of Coriolus versicolor mycelia and a concentrate of a Coriolus versicolor culture in a manner similar to that of Example 9. The powder and the concentrate were 5.5 g and 910 mL in mass and volume, respectively.

Mushroom mycelia obtained in Examples 9 to 11 were quantitatively analyzed for mineral contents as follows.

EXPERIMENTAL EXAMPLE 1

Chromium Contents of Mushroom Mycelia

Chromium was quantitatively measured in the Ganoderma lucidum mycelia cultured in the same manner as in Example 9 (test group 1) and cultured in a the same manner as in Example 9, except for not using chromium (control group). Test group 1 was measured to have more chromium than did Control group, as seen in Table 1, below.

TABLE 1

| Chromium Contents of Ganoderm lucidum mycelia | |
|---|---|
| Control Group (mg/kg) | Test Group 1 (mg/kg) |
| 1.3 (T.C.P.) | 677.8 (I.C.P.) |

EXPERIMENTAL EXAMPLE 2

Selenium Contents of Mushroom Mycelia

Selenium was quantitatively measured in the Ganoderma lucidum mycelia cultured in the same manner as in Example 10 (test group 2) and cultured in a the same manner as in Example 9, except for not using chromium (control group) Test group 2 was measured to have more selenium than did Control group, as seen in Table 2, below.

TABLE 2

| Selenium Contents of Ganoderm lucidum mycelia | |
|---|---|
| Control Group (mg/kg) | Test Group 2 (mg/kg) |
| 1.9 (I.C.P.) | 3,662.4 (I.C.P.) |

EXAMPLE 12

Preparation of Functional Beverage Using Hot-Water Extract of Mushroom Mycelia 3 g of the Ganoderm lucidum mycelia powder obtained in Example 9 (chromium content about 2 mg) and 0.15 g of the Ganoderm lucidum mycelia obtained in Example 10 (chromium content about 0.55 mg) were mixed with 1.5 liters of a Ganoderm lucidum culture obtained in the same manner as in Example 9 or 10, except for using neither chromium nor selenium. The mixture was concentrated to 1 liter under vacuum or by heating, followed by filtration.

The beverage thus obtained was provided to five patients who suffered from diabetes mellitus and an examination was made of the taste and medicinal effects of the beverage. All subjects answered that the beverage had an excellent taste. Blood glucose levels were monitored for three weeks while the subjects were allowed to drink 100 mL of the beverage once per day for the same time period. Of them, the average blood glucose level of one patient was measured to be decreased by 35%, compared to his usual average value, the average blood glucose level of another patient by 20%, and average blood glucose levels of two persons by 14%. The patient whose average blood glucose level was decreased to as low as 65% compared to his usual values could decrease his usual insulin dosage. The patient from whom no improvements in blood glucose level were obtained had shown significantly undulating blood glucose levels. However, his blood cholesterol level was improved at 23%. Therefore, the beverage of the present invention was medicinally effective for patients who suffer from diabetes mellitus or hypercholesterolemia. Also, medicinally effects were reported from patients who suffered from hyperlipidemia, obesity, asthma, or insomnia after they had drunk the beverage of the present invention.

EXAMPLE 13

Raising of Ducks with Mushroom Culture 300 mL of the Ganoderm lucidum mycelium culture containing chromium, obtained in Example 9 and 300 mL of the Ganoderm lucidum mycelium culture containing selenium, obtained in Example 10 were mixed with 1.2 liters of a Ganoderm lucidum culture obtained in the same manner as in Example 9 or 10, except for using neither chromium nor selenium, to give 1.8 liters of a mushroom culture 1. Separately, 600 mL of the Ganoderm lucidum mycelium culture containing chromium, obtained in Example 9 and 600 mL of the Ganoderm lucidum mycelium culture containing selenium, obtained in Example 10 were mixed with 600 mL of a Ganoderm lucidum culture obtained in the same manner as in Example 9 or 10, except for using neither chromium nor selenium, to give 1.8 liters of a mushroom culture 2.

50 ducks (Cherry-Berry, England: Avg. weight 400 g), which were 21 days old, were initially fed daily from a 1.8 liter Ganoderm lucidum culture 1, along with their daily amount of feedstuff. From day 17, 1.8 liters of the Ganoderm lucidum culture 2 was mixed with the daily feedstuff, instead of the Ganoderm lucidum culture 1. As a control group, 50 ducks (Avg. weight 400 g) were fed with feedstuffs to which no Ganoderm lucidum cultures were added. 24 days into the experiment, ducks in both the test group and the control group were measured to weigh 2.1 kg on average. The daily amount of the feedstuff per duck increased from 250 g in the early stage to 1 kg in the late stage, with the total feedstuff for one duck over 24 days amounting to 9 kg on average. As for the Ganoderm lucidum cultures, they were consumed at a daily amount of 36 ml per duck and at a total amount of 900 ml per duck in all. Usually used was the feedstuff which contained 17.5% or more of crude proteins, 25% of crude lipids, 6% of crude fibrous materials, 8% of crude ash, 0.7% of calcium, and 0.6% of phosphorous.

EXPERIMENTAL EXAMPLE 3

Effect on Quality and Taste of Duck Meat

An examination was made of the quality and taste of duck meat (test group and control group). The meat of the test group was more moist and smoother and better in taste than that of the control group. Additionally, the meat of the test group did not give off any offensive odors and was observed to be much smaller in fat content when being roasted. Also, the meat of the ducks of the test group was sitiologically improved in terms of lipid distribution: unsaturated lipids were increased while saturated lipids were decreased.

EXPERIMENTAL EXAMPLE 4

Cholesterol Content of Duck Meat

A measurment was made of the cholesterol contents in the meats of the duck raised in Example 13 (test group and control group). The cholestrol content of the meat of the test group was measured to be 7.4% lower than that of the control group, as shown in Table 3, below.

TABLE 3

| Cholesterol Content of Duck Meat | |
| --- | --- |
| Control Group (mg/100 g) | Test Group (mg/100 g) |
| 68.7 | 63.6 |

EXPERIMENTAL EXAMPLE 5

Chromium Content of Duck Meat

The meats of the ducks bred in Example 13 (test group and control group) were measured for chromium content. As shown in Table 4, below, the chromium content of the meat of the test group was about four-fold greater than that of the control group.

TABLE 4

| Chromium Content of Duck Meat | |
| --- | --- |
| Control Group (mg/kg) | Test Group (mg/kg) |
| 0.06 (I.C.P) | 0.24 (T.C.P) |

EXPERIMENTAL EXAMPLE 6

Selenium Content of Duck Meat

The meats of the ducks bred in Example 13 (test group and control group) were measured for selenium content. As shown in Table 5, below, the selenium content of the meat of the test group was about 2.3-fold greater than that of the control group.

TABLE 5

| Selenium Content of Duck Meat | |
| --- | --- |
| Control Group (mg/kg) | Test Group (mg/kg) |
| 0.27 (I.C.P) | 0.61 (I.C.P) |

Taken together, the results obtained in the above examples demonstrate that the duck meat of the present invention can be used as a food for patients who suffer from diabetes mellitus, as well as adult diseases, such as hypercholesterolemia, hyperlipidemia, and obesty.

As described hereinbefore, mushroom mycelia can be cultured at low cost by using the water from the washing of grains as a culture medium in accordance with the present invention. Additionally, the use of the water from the washing of grains in culturing mushroom mycelia results in preventing the water pollution caused by wasting the water from houses and grain-packing plants. Mushroom mycelia rich in trace minerals can be also cultured by use of a broth supplemented with trace minerals such as chromium, selenium and germanium and are used for producing functional beverages effective for the treatment and prophylaxis of adult diseases such as diabetes mellitus. Further, when ducks are fed with the mushroom cultures of the present invention, the meat is improved in quality and taste and has low cholesterol content. Consequently, the present invention finds various applications in the food industry.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A composition having blood glucose level reduction activity, comprising a chromium-rich mushroom mycelium powder in an amount of 0.001 to 1% by weight which is prepared by a method for producing mushroom mycelia comprising the steps of:

a) seed-culturing a mushroom mycelium selected from the group consisting of *Ganoderma lucidum, Coriolus versicolor, Schizophyllum commune, Pleurotus ostreatus, Pleurotus sajor-caju, Lentinus edodes, Flammulina velutipes*, Auricularia spp., *Grifola fromdosa, Ramaria botrytis* (Fr.) Rick, and *Pholiota nameko;* b) preparing a culture medium by adding an amount of 100 to 1200 mg/L of chromium to a liquid medium containing rice bran in an amount of 0.5% by weight and wheat in an amount of 0.2 to 2% by weight;

c) inoculating the cultured mushroom mycelium into the culture medium of step b) and incubating the culture medium at 20 to 30° C. for 10 to 20 days upon fix culturing or for 5 to 10 days upon shake culturing; and d) filtering and concentrating said cultured solution, and then obtaining the resulting chromium-rich mushroom mycelium powder.

* * * * *